US007795169B2

(12) United States Patent
Fischer et al.

(10) Patent No.: US 7,795,169 B2
(45) Date of Patent: Sep. 14, 2010

(54) PROCESS FOR PREPARING CYANOPYRIDINES AND SUITABLE CATALYSTS THEREFOR

(75) Inventors: Achim Fischer, Aschaffenburg (DE); Andreas Martin, Berlin (DE); Bernhard Lucke, Berlin (DE); Venkata Kalevaru, New Nallakunta Hyderabad (IN); Christoph Weckbecker, Grundau-Lieblos (DE); Klaus Huthmacher, Geinhausen (DE)

(73) Assignee: Vertellus Specialties Inc., Indianapolis, IN (US)

( * ) Notice: Subject to any disclaimer, the term of this patent is extended or adjusted under 35 U.S.C. 154(b) by 912 days.

(21) Appl. No.: 10/566,868

(22) PCT Filed: Jul. 30, 2004

(86) PCT No.: PCT/US2004/024939

§ 371 (c)(1),
(2), (4) Date: Jan. 16, 2007

(87) PCT Pub. No.: WO2005/016505

PCT Pub. Date: Feb. 24, 2005

(65) Prior Publication Data

US 2007/0117984 A1 May 24, 2007

(30) Foreign Application Priority Data

Aug. 2, 2003 (DE) ................. 103 35 454

(51) Int. Cl.
*B01J 31/00* (2006.01)
*B01J 27/24* (2006.01)
*B01J 27/198* (2006.01)
*B01J 27/188* (2006.01)
*B01J 27/19* (2006.01)
*B01J 27/185* (2006.01)
*B01J 27/182* (2006.01)
*B01J 23/00* (2006.01)
*C07D 211/78* (2006.01)
*C07D 211/90* (2006.01)
*C07D 213/84* (2006.01)

(52) U.S. Cl. ............ 502/209; 502/167; 502/200; 502/210; 502/211; 502/213; 502/214; 502/312; 502/353; 546/286

(58) Field of Classification Search ........... 502/167, 502/200, 209–211, 213, 214, 312, 353; 546/286
See application file for complete search history.

(56) References Cited

U.S. PATENT DOCUMENTS

| 3,180,871 | A | * | 4/1965 | Hargrave | 546/252 |
| 3,970,657 | A | * | 7/1976 | Elion et al. | 546/286 |
| 4,111,832 | A | * | 9/1978 | Rohbock et al. | 502/24 |
| 4,447,612 | A | * | 5/1984 | Beschke et al. | 546/285 |
| 4,482,719 | A | * | 11/1984 | Helmut et al. | 546/286 |
| 4,603,207 | A | | 7/1986 | DiCosimo | |
| 4,778,890 | A | * | 10/1988 | Shimizu et al. | 544/336 |
| 4,963,687 | A | | 10/1990 | Saito et al. | |
| 5,028,713 | A | * | 7/1991 | DiCosimo et al. | 546/286 |
| 5,432,141 | A | * | 7/1995 | Brazdil et al. | 502/311 |
| 5,693,587 | A | * | 12/1997 | Brazdil et al. | 502/353 |
| 5,892,049 | A | * | 4/1999 | Hippel et al. | 546/286 |
| 5,910,465 | A | * | 6/1999 | Rao et al. | 502/209 |
| 5,952,508 | A | * | 9/1999 | Rao et al. | 546/286 |
| 6,118,003 | A | * | 9/2000 | McAteer et al. | 546/286 |

FOREIGN PATENT DOCUMENTS

| DE | 241903 | | 1/1987 |
| EP | 0 301 540 | | 2/1989 |
| EP | 0726092 | | 1/1996 |
| EP | 1 069 108 | | 1/2001 |
| EP | 1 113 001 | | 7/2001 |
| IN | 138052 | * | 11/1975 |
| IN | 190431 | * | 7/2003 |
| JP | 07 434673 B | | 9/1974 |
| WO | 2004/087310 A1 | * | 10/2004 |
| WO | 2005/016505 A2 | * | 2/2005 |

OTHER PUBLICATIONS

"Ammoxidation and oxidation of substituted methyl aromatics on vanadium-containing catalysts," Andreas Martin et al. Catalysis Today 57 (2000), pp. 61-70.*
"Defined vanadium phosphorus oxides and their use as highly effective catalyst in ammoxidation of methyl aromatics," Andreas Martin et al. Catalysis Today 78 (2003), pp. 311-317.*
"Ammoxidation of Methylaromatics over NH4+-containing Vanadium Phosphate Catalysts—New Mechanistic Insights," Andreas Martin et al. Heterogenous Catalyst and Fine Chemicals IV (1997), pp. 377-384.*
"Kinetics of Vapour-Phase Ammoxidation of 3-Methylpyridine over a Promoted V2O5-Al2O3 Catalyst," Satya Kumar et al. Chemical Engineering Science vol. 35 (1980), pp. 1425-1441.*
"Study on Ammoxidation of Heteroaromatic Compounds to Prepare Aromatic Nitriles," Yu Peng et al. College of Chemistry and Molecular Sciences, Wuhan University, Hubei, China (date not available).*
Manohar, B., et al.; "Ammoxidation of 3-Picoline to Nicotinonitrile over Vanadium Phosphorous Oxide-Based Catalysts"; J. Chem. Tech. and Biotech.; Feb. 1, 1998; vol. 71, No. 2, pp. 141-146; Blackwell Scientific; Oxford, GB.

(Continued)

*Primary Examiner*—Patricia L Hailey
(74) *Attorney, Agent, or Firm*—William R. Lyon; Ice Miller LLP

(57) ABSTRACT

The invention relates to a method for the manufacture of cyanopyridines from methylpyridines by their conversion with ammonia and oxygen and catalysts suitable therefor which contain further transition metals in addition to vanadium and phosphorus.

6 Claims, No Drawings

OTHER PUBLICATIONS

Takashi, Ohara; Chemical Abstracts (1975); vol. 82, No. 19; Abstract No. 125132u; p. 536, col. 1; Columbus, Ohio, US.

Chemical Abstracts (1980); vol. 92, No. 5; Abstract No. 128741j; p. 684, col. 1; Columbus, Ohio, US.

Supplemental Search Report from European Patent Office; Sep. 5, 2008.

Communication from European Patent Office regarding patents JP 074346738, and IN 138052A; Oct. 13, 2008.

First Office Action from Chinese Intellectual Property Office; Dec. 14, 2007.

First Examination Report from Government of India Patent Office; Jul. 19, 2007.

* cited by examiner

PROCESS FOR PREPARING CYANOPYRIDINES AND SUITABLE CATALYSTS THEREFOR

CLAIM OF PRIORITY

The present application is a U.S. National Application of PCT/US2004/024939, filed Oct. 8, 200, which claims priority to German Patent Application number 103 35 454,9, filed Aug. 2, 2003, the contents of which are herein incorporated by reference.

DESCRIPTION

The invention relates to a method for the manufacture of cyanopyridines and catalysts suitable therefor which contain vanadium and phosphorus.

Several methods for the manufacture of cyanopyridines from methylpyridines by the reaction with ammonia and oxygen are known. They are distinguished by the reaction conditions and in particular by the catalysts. Of these methods only those which have a very good space-time-yield and simultaneously a high selectivity are of significance for use on a commercial scale.

It is known from EP 0 726 092 B1 that the requirements are satisfied by catalyst systems of the general summation formula

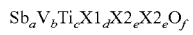

These catalysts are however quite complicated and expensive to manufacture.

It is known from DE 198 04 839 A1 and from DD 241 903 A1 that catalysts of the formula $(NH_4)_2(VO)_3(P_2O_7)_2$ or $(VO)_2P_2O_7$ belong to the class of VPO catalysts which can be used for the ammoxidation of aromatic compounds. These catalysts require relatively high reaction temperatures of more than 440° C. in order to achieve conversions greater than 90%.

The object of the present invention is to develop a method for the manufacture of cyanopyridines through the catalytic reaction of methylpyridines with ammonia and oxygen at elevated temperature while using VPO catalysts which lead to a very good space-time-yield (at high conversion levels) and selectivity at reactor temperatures up to 440° C. and which are simple and reproducible to manufacture.

This object is satisfied by VPO catalysts of the general formula

- a=0.1-2.5
- b=0-3.0, in particular 0.001-3.0
- c=0.1-10
- d=depends on the valency of the other elements
- e=5-100 (% by weight)
- f=95-0 (% by weight), in particular 95-5 with the provision that b and f are not simultaneously 0
- X=Cr, Mo, W, Fe, Ru, Co, Rh, Ir, Ni, Pd, Pt, Zn or Nb
- Y=cyclic nitrogen compound,
- Z=$SiO_2$, $Al_2O_3$, $ZrO_2$ or $TiO_2$ or their mixtures, which can be manufactured in that one brings vanadium pentoxide ($V_2O_5$) and 80 to 85% phosphoric acid to a reaction in an organic medium with reflux conditions, filters off the catalyst precursor which forms, dries it at 80° C. to 140° C. and subsequently calcines it preferably for 1.5 to 4 h at 300° C. to 600° C., more preferably at 350° C. to 480° C., flows a gas consisting of inert gas such as for example argon, helium or nitrogen which is saturated with the vapor of a cyclic nitrogen compound at a temperature of 0 to 80° C., in particular 15 to 45° C. over the vanadium phosphate so obtained at a temperature of 100 to 300° C., in particular 160 to 250° C., for 0.1 to 10 hours, in particular 0.5 to 3 hours and subsequently cools it down.

The flow rate preferably amounts to 5-20 l/h.

After the cooling to room temperature the catalyst contains 0.1 to 5% by weight, in particular 0.5 to 3% by weight of the organic cyclic nitrogen compound, predominantly bound as cation.

The organic cyclic nitrogen compounds are preferably 6-membered rings such as for example pyridine, quinoline, pyridazine, pyrimidine, pyrazine and in particular picoline (3-methylpyridine).

The organic medium consists in general of the mixture of an aromatic alcohol and an aliphatic alcohol in the volume ratio 2:1 to 1:3, in particular 1:1 to 1:2. Benzyl alcohol and benzyl alcohols illustratively bearing 1 to 3 alkyl substituents, each containing 1 to 3 C-atoms, preferred are methyl groups, are suitable as cyclic alcohols. $C_2$-$C_8$ alcohols also with branched chains, in particular n-butanol, are used as aliphatic alcohols.

In this mixture $V_2O_5$ and phosphoric acid are present at the start of the reaction in a molar V:P ratio of 1:0.1 to 1:2.5, in particular 1:0.7 to 1:1.5.

In order to provide the catalyst with further transition metal oxides or mixed oxides which are active as promoters, aqueous or alcoholic solutions of salts of these transition metals X are manufactured. These are preferably such with anions, such as carbonate, nitrate, oxalate or acetate which are removed by heat treatment from the solid body. With these solutions the optionally dried catalyst precursor is impregnated and the excess solution is separated off.

The impregnated catalyst precursor is then dried at 80 to 140° C. for 6 to 24 h and is optionally formed prior to the calcining.

A support material is advantageously mixed with the impregnated or non-impregnated powder, which is in general $SiO_2$, $TiO_2$, $Al_2O_3$ or $ZrO_2$ or mixtures thereof.

The powder is mixed intimately in the desired quantity, generally in the quantity ratio 20:1 to 1:20 with the support component and is ground in a customary mill.

The mixture that is obtained is subsequently calcined at a temperature of 300° C. to 600° C., preferably at 350 to 480° C. for up to 48 h. For this purpose one advantageously uses a nitrogen/oxygen mixture in the composition 1:0.1 to 1:10.

In any event the introduction of the organic cyclic nitrogen compounds into the catalyst takes place after the calcining before the start of the actual catalytic conversion. The method for the manufacture of the catalyst is likewise the subject of the invention.

The catalyst can be used in all suitable reactors for carrying out a heterogeneously catalyzed gas phase reaction. Thus, for example, a continuous solid bed reactor, a stirring vessel, a fixed-bed reactor, a moving bed reactor, or a slurry-phase reactor can be used.

The catalyst is preferably used in methods for the manufacture of cyanopyridines, illustratively 3-cyanopyridine, by the catalytic conversion of a methyl pyridine, illustratively 3-methylpyridine, ammonia and oxygen at a temperature up to 440° C., in particular up to 400° C.

The methods described in EP 0 059 414 B1, in EP 0 070 395 B1 and EP 0 726 092 A1 belong, for example, to the manufacturing methods for 3-cyanopyridine.

In accordance with EP 0 059 414 B1 the conversion of 3-methylpyridine with ammonia and oxygen to 3-cyanopyridine takes place in normal manner in the gas phase. For the selection of the reaction conditions a wide scope is present. The conversion is principally effected without the application of pressure or at a low over-pressure of up to about 3 bar at temperatures between about 320 and 460° C., preferably temperatures between 340 and 440° C. The oxygen that is required can be supplied with advantage as air and water vapor can also be admixed to the gases. The quantity ratio of 3-methylpyridine to ammonia, oxygen, or air and optionally to water vapor can be selected in wide limits. In general it is expedient to use, for each mole of 3-methylpyridine, about 2 to 10 moles, preferably 3 to 8 moles ammonia, about 10 to 40 moles, preferably 25 to 35 moles, of air and approximately 0 to 10 moles, preferably 0 to 8, moles of water vapor. For each liter of bulk volume of the catalyst and per hour approximately 1 to 3 moles of 3 methylpyridine is expediently fed into the reactor.

In the examples % signifies percentages by weight so far as nothing different is stated.

The following terms are used in the following examples:
Conversion=(moles of converted hydrocarbon/moles of hydrocarbon used)*100%
Yield=(moles of produced product/moles of hydrocarbon used)*100%
GHSV=gas hourly space velocity=(the volume of the fed-in gas/time×bulk volume of the catalyst) [1/hl=1/h]
Selectivity=(yield/conversion)*100

EXAMPLES

Catalyst Manufacture

Example 1

Catalyst A, Comparative Example

In accordance with the statements in Inorg. Chem., 23 (1984) 1308, the hemihydrate of the oxovanadium(IV)-hydrogenphosphate $VOHPO_4$-$0.5H_2O$ is manufactured in the aqueous medium. This catalyst precursor was dried at 120° C. for 24 h and converted into the oxovanadium diphosphate $(VO)_2P_2O_7$ by 3 hour calcining at 450° C. in nitrogen/oxygen mixtures.

Example 2

Catalyst B

The oxovanadium diphosphate can be manufactured in organic solvents by stirring a mixture of 0.1 mole (18.2 g) $V_2O_5$ suspended in 110 ml n-butanol and 73 ml benzyl alcohol with refluxing for 3 h. Subsequently, stirring is continued over night at room temperature, thereafter 85 phosphoric acid is added in a stoichiometrically adequate quantity and stirring is carried out again for a further 2 h with refluxing and the catalyst precursor formed is filtered off at room temperature, is washed several times with ethanol and is finally dried for 24 h at 120° C. After 3 h of calcining at 450° C. in the nitrogen/oxygen mixtures one obtains the oxovanadium diphosphate $(VO)_2P_2O_7$, as in example 1.

Example 3

Catalyst C

In accordance with this example the manufacture of supported catalysts takes place:

For this purpose one terminates the syntheses described in examples 1 and 2 upon isolation of the catalyst precursor (i.e. before the final calcining). Titanium dioxide (anatase) powder (B.E.T. surface ca. 100 m$^2$/g) is mixed in the weight ratio 3:1 with the powder of the catalyst precursor in accordance with example 1 or 2 ($VOHPO_4$-$0.5H_2O$) and is ground intimately in an agate stone mill and also subsequently in an electrical mill (5-10 min). Thereafter the catalyst composition is pressed, is broken and a screen fraction of ca. 1-1.25 mm in diameter is recovered. This fraction is calcined for 3 h in nitrogen/oxygen mixtures at 450° C. and contains a vanadium phosphate, mainly as $(VO)_2P_2O_7$.

Example 4

Catalyst D

Catalysts in accordance with example 3 can also be mixed with transition metal promoters. For this purpose the catalyst precursor of example 1 or 2 is promoted before the mixture with the support component takes place. The manufacture of the promoted catalyst precursor is described in the following for an iron promotion:

0.1 moles of the catalyst precursor ($VOHPO_4$–$0.5H_2O$) obtained in accordance with example 1 or 2 respectively are impregnated with 0.05 moles iron(III)-acetate (dissolved in ethanol or water). Thereafter the solvent is evaporated and the residue is dried at 120° C. for 16 h and subsequently calcined.

Example 5

Catalyst E

The catalyst precursor manufactured in example 4 is mixed as described in example 3 in the ratio 1:3 with titanium dioxide (anatase) powder and is ground as described. After drying and calcining (as in example 3) one obtains a supported and promoted catalyst which contains a vanadium phosphate, mainly as $(VO)_2P_2O_7$.

Example 6

Catalyst F

The oxovanadium phosphate of example 2 with a particle size range of 1-1,25 mm is placed in a reaction tube and heated up to 200° C. in steps of 10° K/min with a gas flow of 10 l/h of argon (saturated at room temperature with 3-picoline) for a period of 2 h. Thereafter cooling to room temperature takes place in the argon stream. The treated catalyst contains as an additional component 3-picoline (predominantly as cation) which can be proven with respect IR-spectra and by elementary analysis. The sample contains ca. 1.5% picoline, predominantly as picolinium cation.

Example 7

Catalyst G

The catalyst support of example 3 is treated with an argon/3-picoline stream as described in example 6. After the treatment the catalyst contains ca. 2% 3-picoline, predominantly as picolinium cation.

Example 8

Catalyst H

The iron promoted support catalyst of example 4 is, as described in example 6, treated with an argon/3-picoline stream. After the treatment of the catalyst contains ca. 2% 3-picoline, predominantly as picolinium cation.

Manufacture of 3-cyanopyridine

Examples 9 to 15

A quartz fixed-bed reactor was loaded with 5 g of catalyst chips mixed 1:1 with corundum. 3-Picoline and optionally water are pumped into the reaction gas stream of air and ammonia and vaporized. The reaction conditions and vapor composition of the gases that are used can be seen in Table 1. Sampling takes place 10 min after the start of the reaction. The reaction products were analyzed by gas chromatography and quantified. The results are likewise set forth in Table 1. The tests 9-12 on non-pre-treated catalysts resulted in a picoline conversion of ca. 50%, 10 min after the start of reaction, whereas it is shown in tests 14-15 that catalysts which predominantly contain picolinium cation following pre-treatment already reach a conversion ≧95% directly after the start of the reaction. The selectivity of the reaction to 3-cyanopyridine is high in each case, at >84%, Comparative Example with Catalyst A A quartz fixed-bed reactor was loaded with 5 g of catalyst A chips mixed 1:1 with corundum. 3-Picoline and optionally water are pumped into the reaction gas stream of air and ammonia and vaporized. The operation took place with the following mole ratio: 3-picoline:ammonia:air:water=1:4.4:28.4:8.5. At a catalyst temperature of 355° C. and a contact time of 1.5 s a 3-picoline conversion of 35% was determined, the yield of nicotinonitrile lay at 29 which corresponds to a selectivity of 84%.

The catalyst was gassed prior to use with a stream containing picoline and the test was carried out subsequently in the manner quoted above.

In a second test the operation took place with the following molar ratio: 3-picoline ammonia:air water=1:4.6:29.4:8.9. At a catalyst temperature of 362° C. and a contact time of 1.5 s a 3-picoline conversion of 43% was determined. The yield of nicotinonitrile lay at 35%, which corresponds to a selectivity of 82%.

| Example | Catalyst | Conversion [Mole %] | Yield [Mole-%] | Selectivity [Mole-%] | CO [Mole-%] | CO$_2$ [Mole-%] |
|---|---|---|---|---|---|---|
| 16 | B | 62 | 55 | 88 | 6 | 4.8 |
| 17 | C | 63 | 57 | 90 | 3 | 4.6 |
| 18 | D | 62 | 56 | 90 | 2 | 4.3 |
| 19 | E | 65 | 60 | 92 | 3 | 4.4 |
| 20 | F | 95 | 80 | 84 | 5 | 5.0 |
| 21 | G | 98 | 84 | 86 | 5 | 4.3 |
| 22 | H | 99 | 99 | 100 | — | — |

It is shown that the picoline conversion for the non-pretreated catalyst has already risen by up to 10%. The pretreated catalysts furthermore show the same high performance as at the start. The used catalysts of examples 16 to 19 now show demonstrable proportions of 3-picoline built into the lattice, as can for example be determined by infrared spectroscopy.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein are incorporated by reference as if fully set forth.

What is claimed is:

1. A VPO catalyst of the general formula:

[V$_1$P$_a$X$_b$(Y)$_c$O$_d$]$_e$[Z]$_f$, in which a=0.1-2.5
b=0-3.0, in particular 0.001-3.0
c=0.1-10
d=depends on the valency of the other elements
e=5-100 (% by weight)

TABLE 1

| Examples | Catalyst | Reaction temperature [° C.] | GHSV [h-1] | Air [MV] | NH$_3$ [MV] | H$_2$O [MV] | Conversion [mole-%] | Yield [mole-%] | Selectivity [Mole-%] | CO [Mole-%] | CO$_2$ [Mole-%] |
|---|---|---|---|---|---|---|---|---|---|---|---|
| 9 | B | 360 | 2300 | 28.4 | 5.6 | 8.2 | 52 | 43.7 | 84 | 0.7 | 4.9 |
| 10 | C | 360 | 2250 | 28.3 | 5.3 | 8.1 | 52 | 46.2 | 89 | 0.3 | 4.7 |
| 11 | D | 350 | 2200 | 29.1 | 5.0 | 8.4 | 53 | 48.9 | 89 | 0.2 | 4.4 |
| 12 | E | 350 | 2200 | 28.9 | 4.4 | 8.5 | 54 | 48.6 | 90 | 0.3 | 4.6 |
| 13 | F | 400 | 2000 | 29.0 | 5.0 | 8.5 | 95 | 80.0 | 84 | 0.6 | 4.9 |
| 14 | G | 350 | 2500 | 29.1 | 4.5 | 8.7 | 97 | 81.3 | 84 | 0.6 | 4.5 |
| 15 | H | 340 | 2000 | 28.6 | 5.7 | — | 99 | 99.0 | 100 | — | — |

MV = molar ratio

Examples 16 to 22

The method as described in the examples 9 to 15 was continued, except that the reaction products are determined after 6 h. Under the same reaction conditions the following results were then obtained f=95-0 (% by weight), in particular 95-5 with the provision that b and f are not simultaneously 0
X=Cr, Mo, W, Fe, Ru, Co, Rh, Ir, Ni, Pd, Pt, Zn or Nb
Y=cyclic nitrogen compound,
Z=SiO$_2$, Al$_2$O$_3$, ZrO$_2$ or TiO$_2$ or their mixtures,
manufactured in accordance with a method in which one carries out the following steps:

a) converting $V_2O_5$ and concentrated phosphoric acid in an organic medium under reflux conditions,
b) separating off catalyst precursor that forms and optionally
c) drying at 80 to 140° C.,
d) impregnating the optionally dried catalyst precursor with an aqueous or alcoholic solution of the metal X, with X having the significance quoted above,
e) separating off excess solution,
f) drying and calcining the impregnated material, and
g) optionally forming the catalyst obtained.

2. The VPO catalyst in accordance with claim 1, characterized in that the catalyst contains $SiO_2$, $Al_2O_3$, $ZrO_2$ or $TiO_2$ or their mixtures as a support.

3. The VPO catalyst in accordance with claim 1, characterized in that the catalyst contains 0.01 to 5% by weight of an organic cyclic nitrogen compound.

4. The VPO catalyst in accordance with claim 3, characterized in that the catalyst contains as the nitrogen compound a compound selected from the group consisting of pyridine, quinoline, pyridazine, pyrimidine, and pyrazine.

5. The VPO catalyst in accordance with claim 3, characterized in that the catalyst contains 3-methylpyridine as the nitrogen compound.

6. A method of manufacture of 3-cyanopyridine, the method comprising the steps of:
providing a VPO catalyst of the general formula:

$[V_1P_aX_b(Y)_cO_d]_e[Z]_f$, in which a=0.1-2.5
b=0-3.0, in particular 0.001-3.0
c=0, 1-10
d=depends on the valency of the other elements
e=5-100 (% by weight)
f=95-0 (% by weight), in particular 95-5 with the provision that b and f are not simultaneously 0
X=Cr, Mo, W, Fe, Ru, Co, Rh, Ir, Ni, Pd, Pt, Zn or Nb
Y=cyclic nitrogen compound,
Z=$SiO_2$, $Al_2O_3$, $ZrO_2$ or $TiO_2$ or their mixtures;
providing 3-methylpyridine;
providing ammonia;
providing oxygen; and
combining the VPO catalyst, 3-methylpyridine, ammonia, and oxygen at temperatures up to 440° C.

* * * * *